US008503707B2

(12) United States Patent
Urso et al.

(10) Patent No.: US 8,503,707 B2
(45) **Date of Patent: *Aug. 6, 2013**

(54) SEALING RETAINER FOR EXTENDED WEAR HEARING DEVICES

(75) Inventors: Richard C Urso, Redwood City, CA (US); Adnan Shennib, Fremont, CA (US); Greg Anderson, Fremont, CA (US); Sunder Ram, San Jose, CA (US); Robert Schindler, San Francisco, CA (US); Ian Day, Fremont, CA (US); James Buckley, San Jose, CA (US)

(73) Assignee: InSound Medical, Inc., Newark, CA (US)

( * ) Notice: Subject to any disclaimer, the term of this patent is extended or adjusted under 35 U.S.C. 154(b) by 600 days.

This patent is subject to a terminal disclaimer.

(21) Appl. No.: 12/646,740

(22) Filed: Dec. 23, 2009

(65) Prior Publication Data

US 2010/0098281 A1 Apr. 22, 2010

Related U.S. Application Data

(60) Division of application No. 11/238,154, filed on Sep. 27, 2005, now Pat. No. 7,664,282, which is a continuation-in-part of application No. 10/693,628, filed on Oct. 25, 2003, now Pat. No. 7,310,426, and a continuation-in-part of application No. 10/052,199, filed on Jan. 16, 2002, now Pat. No. 7,215,789, which is a continuation of application No. 09/327,717, filed on Jun. 8, 1999, now Pat. No. 6,473,513.

(51) Int. Cl.
*H04R 25/00* (2006.01)
*A61B 7/02* (2006.01)

(52) U.S. Cl.
USPC ............................ 381/328; 381/322; 181/135

(58) Field of Classification Search
USPC ................. 181/128, 130, 135; 381/312, 320, 381/322, 328
See application file for complete search history.

(56) References Cited

U.S. PATENT DOCUMENTS

| | | | |
|---|---|---|---|
| 3,061,689 | A | 10/1962 | McCarrell et al. |
| RE26,258 | E | 8/1967 | Martin |
| 3,414,685 | A | 12/1968 | Geib et al. |
| 3,527,901 | A | 9/1970 | Geib |

(Continued)

OTHER PUBLICATIONS

Ballachandra, The Human Ear Canal, Singular Publishing, 1995, pp. 195.

(Continued)

*Primary Examiner* — Jesse Elbin
(74) *Attorney, Agent, or Firm* — Henricks, Slavin & Holmes LLP

(57) ABSTRACT

An embodiment provides a seal for retaining a hearing device within the ear canal comprising a curved shell having an opening at a shell apex portion. The shell defines a cavity for retention of a device component. An interior surface of a shell wall has a scalloped shape configured to distribute compressive forces applied to the shell perimeter such that when the shell is positioned in the canal, the shell wall conforms to the shape of the canal to maintain an acoustical seal between a shell exterior surface and the canal walls. The scalloped shape can be configured to produce a substantially constant amount of inward deformation of a shell wall independent of a force application point on a shell perimeter. The shell can include a coating to retain the seal in the canal and/or to promote asparagine growth into the coating to fastenly retain the seal in the canal.

24 Claims, 19 Drawing Sheets

U.S. PATENT DOCUMENTS

| | | | |
|---|---|---|---|
| 3,594,514 | A | 7/1971 | Wingrove |
| 3,764,748 | A | 10/1973 | Branch et al. |
| 3,783,201 | A | 1/1974 | Weiss et al. |
| 3,865,998 | A | 2/1975 | Weiss et al. |
| 3,870,832 | A | 3/1975 | Fredrickson |
| 3,882,285 | A | 5/1975 | Nunley et al. |
| 4,442,917 | A | 4/1984 | Johnson |
| 4,539,440 | A | 9/1985 | Sciarra |
| 4,606,329 | A | 8/1986 | Hough |
| 4,607,720 | A | 8/1986 | Hardt |
| 4,628,907 | A | 12/1986 | Epley |
| 4,639,556 | A | 1/1987 | Hardt et al. |
| 4,680,799 | A | 7/1987 | Henneberger |
| 4,756,312 | A | 7/1988 | Epley |
| 4,776,322 | A | 10/1988 | Hough et al. |
| 4,817,607 | A | 4/1989 | Tatge |
| 4,830,139 | A | 5/1989 | Cirillo |
| 4,840,178 | A | 6/1989 | Heide et al. |
| 4,870,688 | A | 9/1989 | Voroba et al. |
| 4,880,076 | A | 11/1989 | Ahlberg et al. |
| 4,937,876 | A | 6/1990 | Biermans |
| 4,957,478 | A | 9/1990 | Maniglia |
| 5,002,151 | A | 3/1991 | Oliveira et al. |
| 5,015,224 | A | 5/1991 | Maniglia |
| 5,015,225 | A | 5/1991 | Hough et al. |
| 5,163,957 | A | 11/1992 | Sade et al. |
| 5,201,007 | A | 4/1993 | Ward et al. |
| 5,220,918 | A | 6/1993 | Heide et al. |
| 5,233,322 | A | 8/1993 | Posey |
| 5,259,032 | A | 11/1993 | Perkins et al. |
| 5,282,858 | A | 2/1994 | Bisch et al. |
| 5,338,287 | A | 8/1994 | Miller et al. |
| 5,390,254 | A | 2/1995 | Adelman |
| 5,401,920 | A | 3/1995 | Oliveira |
| 5,425,104 | A | 6/1995 | Shennib |
| 5,430,801 | A | 7/1995 | Hill |
| 5,456,654 | A | 10/1995 | Ball |
| 5,531,787 | A | 7/1996 | Lesinski et al. |
| 5,554,096 | A | 9/1996 | Ball |
| 5,572,594 | A | 11/1996 | Devoe et al. |
| 5,624,376 | A | 4/1997 | Ball et al. |
| 5,654,530 | A | 8/1997 | Sauer et al. |
| 5,659,621 | A | 8/1997 | Newton |
| 5,682,020 | A | 10/1997 | Oliveira |
| 5,701,348 | A | 12/1997 | Shennib et al. |
| 5,701,438 | A | 12/1997 | Banns |
| 5,742,692 | A | 4/1998 | Garcia |
| 5,811,896 | A | 9/1998 | Grad |
| 5,825,896 | A | 10/1998 | Leedom |
| 5,833,626 | A | 11/1998 | Leysieffer |
| 5,887,070 | A | 3/1999 | Iseberg et al. |
| 5,949,895 | A | 9/1999 | Ball et al. |
| 5,982,908 | A | 11/1999 | Bauman |
| 6,058,198 | A | 5/2000 | Aceti |
| 6,094,493 | A | 7/2000 | Borowsky et al. |
| 6,137,889 | A | 10/2000 | Shennib et al. |
| 6,205,227 | B1 | 3/2001 | Mahoney et al. |
| 6,208,741 | B1 | 3/2001 | Shennib et al. |
| 6,212,283 | B1 | 4/2001 | Fletcher |
| 6,229,900 | B1 | 5/2001 | Leenen |
| 6,310,961 | B1 | 10/2001 | Oliveira et al. |
| 6,359,993 | B2 | 3/2002 | Brimhall |
| 6,408,081 | B1 | 6/2002 | Boesen |
| 6,473,511 | B1 | 10/2002 | Aceti et al. |
| 6,473,513 | B1 | 10/2002 | Shennib et al. |
| 6,595,796 | B1 | 7/2003 | Koegel |
| 6,620,110 | B2 | 9/2003 | Schmid |
| 6,643,378 | B2 | 11/2003 | Schumaier |
| 6,648,813 | B2 | 11/2003 | Zilberman et al. |
| 6,658,126 | B1 | 12/2003 | Stern |
| 6,671,381 | B1 | 12/2003 | Lux-Wellenhof |
| 6,754,357 | B2 | 6/2004 | McIntosh et al. |
| 6,940,988 | B1 | 9/2005 | Shennib et al. |
| 7,016,511 | B1 | 3/2006 | Shennib |
| 7,130,437 | B2 | 10/2006 | Stonikas et al. |
| 7,310,426 | B2 | 12/2007 | Shennib et al. |
| 7,403,629 | B1 | 7/2008 | Aceti et al. |
| 7,580,537 | B2 | 8/2009 | Urso et al. |
| 7,664,282 | B2 | 2/2010 | Urso et al. |
| 2004/0017922 | A1 | 1/2004 | Bachler et al. |
| 2004/0161445 | A1 | 8/2004 | Bulk et al. |
| 2004/0165742 | A1 | 8/2004 | Shennib et al. |
| 2006/0067551 | A1 | 3/2006 | Cartwright et al. |
| 2006/0098833 | A1 | 5/2006 | Juneau et al. |
| 2006/0291683 | A1 | 12/2006 | Urso et al. |

OTHER PUBLICATIONS

Chasin, CIC Handbook, Singular Publishing Group, Inc. (1997), pp. 5, 9-14, 17-18, 27-28, 44, 56-58, and 65-66.

Oliveira, et al, "The Wax Problem: Two New Approaches," The Hearing Journal, 1993; 46(8: 41-46, 48.

Siemens Hearing Instruments, Inc., General Information for Hearing aid Users, Mar. 98, p. 1-14.

Valente, Strategies for Selecting and Verging Hearing Aid Fittings, Theme Medical Publishing. pp. 255-256, 1994.

Widex Hearing Aid Co, Users's Instructions, SENSO CIC and Mini Canal. Feb. 1997, pp. 2-27.

SEALING RETAINER FOR EXTENDED WEAR HEARING DEVICES

CROSS-REFERENCES TO RELATED APPLICATIONS

This application is a divisional of U.S. patent application Ser. No. 11/238,154, filed Sep. 27, 2005, now U.S. Pat. No. 7,664,282, which is a continuation-in-part of U.S. patent application Ser. No. 10/052,199, filed Jan. 16, 2002, now U.S. Pat. No. 7,215,789, titled "Disposable Extended Wear Canal Hearing Device," which was a continuation of U.S. patent application Ser. No. 09/327,717, filed Jun. 8, 1999, now U.S. Pat. No. 6,473,513, titled "Extended Wear Canal Hearing Device," both of which are fully incorporated herein by reference.

This application is also a continuation-in-part of U.S. patent application Ser. No. 10/693,628, filed Oct. 25, 2003, now U.S. Pat. No. 7,310,426, titled "Inconspicuous Semi-Permanent Hearing Device," which was a continuation of U.S. patent application Ser. No. 09/199,669, filed Nov. 25, 1998, now U.S. Pat. No. 6,940,988, titled "Semi-Permanent Canal Hearing Device," both of which are fully incorporated herein by reference.

BACKGROUND OF THE INVENTION

1. Field of the Invention

Embodiments of invention relate to hearing devices. More specifically embodiments of the invention relate to sealing retainers for improving the durability and comfort of continuous or extended wear hearing aids.

Since many hearing aid devices are adapted to be fit into the ear canal, a brief description of the anatomy of the ear canal will now be presented for purposes of illustration. While, the shape and structure, or morphology, of the ear canal can vary from person to person, certain characteristics are common to all individuals. Referring now to FIGS. 1-2, the external acoustic meatus (ear canal) is generally narrow and contoured as shown in the coronal view in FIG. 1. The ear canal 10 is approximately 25 mm in length from the canal aperture 17 to the center of the tympanic membrane 18 (eardrum). The lateral part (away from the tympanic membrane) of the ear canal, a cartilaginous region 11, is relatively soft due to the underlying cartilaginous tissue. The cartilaginous region 11 of the ear canal 10 deforms and moves in response to the mandibular (jaw) motions, which occur during talking, yawning, eating, etc. The medial (towards the tympanic membrane) part, a bony region 13 proximal to the tympanic membrane, is rigid due to the underlying bony tissue. The skin 14 in the bony region 13 is thin (relative to the skin 16 in the cartilaginous region) and is more sensitive to touch or pressure. There is a characteristic bend 15 that roughly occurs at the bony-cartilaginous junction 19 (referred to herein as the bony junction), which separates the cartilaginous 11 and the bony 13 regions. The magnitude of this bend varies among individuals.

A cross-sectional view of the typical ear canal 10 (FIG. 2) reveals generally an oval shape and pointed inferiorly (lower side). The long diameter ($D_L$) is along the vertical axis and the short diameter ($D_S$) is along the horizontal axis. These dimensions vary among individuals.

Hair 5 and debris 4 in the ear canal are primarily present in the cartilaginous region 11. Physiologic debris includes cerumen (earwax), sweat, decayed hair, and oils produced by the various glands underneath the skin in the cartilaginous region. Non-physiologic debris consists primarily of environmental particles that enter the ear canal. Canal debris is naturally extruded to the outside of the ear by the process of lateral epithelial cell migration (see e.g., Ballachanda, The Human Ear Canal, Singular Publishing, 1995, pp. 195). There is no cerumen production or hair in the bony part of the ear canal.

The ear canal 10 terminates medially with the tympanic membrane 18. Laterally and external to the ear canal is the concha cavity 2 and the auricle 3, both also cartilaginous. The junction between the concha cavity 2 and the cartilaginous part 11 of the ear canal at the aperture 17 is also defined by a characteristic bend 12 known as the first bend of the ear canal.

First generation hearing devices were primarily of the Behind-The-Ear (BTE) type. However, they have been largely replaced by In-The-Canal (ITC) hearing devices are of which there are three types. In-The-Ear (ITE) devices rest primarily in the concha of the ear and have the disadvantages of being fairly conspicuous to a bystander and relatively bulky to wear. Smaller In-The-Canal (ITC) devices fit partially in the concha and partially in the ear canal and are less visible but still leave a substantial portion of the hearing device exposed. Recently, Completely-In-The-Canal (CIC) hearing devices have come into greater use. These devices fit deep within the ear canal and can be essentially hidden from view from the outside.

In addition to the obvious cosmetic advantages, CIC hearing devices provide, they also have several performance advantages that larger, externally mounted devices do not offer. Placing the hearing device deep within the ear canal and proximate to the tympanic membrane (ear drum) improves the frequency response of the device, reduces the occurrence of the occlusion effect and improves overall sound fidelity.

However, despite their advantages, many CIC hearing devices continue to have performance issues including retention in the ear canal and acoustic feedback. Seals incorporated onto CIC devices have been used to prevent oscillatory feedback which occurs when there is acoustic leakage from the output of the hearing aid receiver through a leakage path which reaches the hearing aid microphone causing sustained oscillation. This oscillatory feedback is manifested by "whistling" or "squealing" which is both bothersome and interferes with communication. Oscillatory feedback is typically alleviated by tightly occluding (sealing) the ear canal between the microphone and the receiver. However, complete sealing can prove difficult, for example, jaw motion of the user may cause deformation of the seal and thus acoustical leakage. During jaw movement the fleshy part moves relative to the bony part so that the hearing aid and/or seal are pressed to one side of the ear canal and a gap may be formed at the other side giving rise to an acoustical leakage path causing feedback. The seal(s) can buckle due to non uniform distribution of forces on the seal and/or when the ear canal deforms resulting in an acoustical leak.

Also, the seal or hearing aid housing may not be sufficiently biocompatible or exert too much force on the ear canal epithelium resulting in one or more of irritation, inflammation, ulceration and/or infection of the epithelium and ear canal as well as thinning of the epithelium. Further, long term effects of wearing aids hearing aid are known to include chronic inflammation and atrophy of the canal epithelium and a gradual remodeling of the bony canal. Besides being uncomfortable, such conditions can require the hearing device to be removed and may actually inhibit or prevent the patient from wearing the hearing aid for extended periods of time until the canal heals. Accordingly, there is a need for a biocompatible seal for a hearing aid to comfortably retain the device in the ear canal on a continuous wear basis while reducing acoustic feedback and the risk of infection and skin ulceration.

BRIEF SUMMARY OF THE INVENTION

Various embodiments of the invention provide systems and assemblies for improving the long term reliability and wearability of extended wear hearing devices including completely in the canal (CIC) hearing aids. Many embodiments provide a seal for improving one or more of the comfort, fit, biocompatibility and performance of CIC hearing aids worn for extended periods including three to six months or longer. Specific embodiments provide a sealing retainer that stabilizes the hearing aid in the ear canal while maintaining the health and integrity of the ear canal including the canal epithelium. Also particular embodiments provide two or more sealing retainers for retaining the hearing aid or other hearing device in the ear canal. In one embodiment, the seal can comprise a first seal configured to be mounted over a first hearing device component, such as a microphone assembly, and a second seal configured to be mounted over a second hearing device component, such as a receiver assembly.

Many embodiment provides a sealing retainer for a CIC hearing aid comprising a hollow curved compliant shell having a centrally placed opening for holding the hearing aid and inner walls having a scalloped or convoluted shape. The shell has a dome like shape configured to fit in the ear canal that can include an oval cross and a medially decreasing taper with respect to a longitudinal axis of the shell. The shell can also include a vent and a sleeve section positioned at an apex of the shell that fits over portions of the body of the hearing aid. These and related embodiments of the retainer can be configured to perform several functions. First, the retainer can be configured to retain and center the hearing aid within the ear canal for long term wear. Retention can be achieved by constructing the retainer from an elastomeric material, such as an elastomeric foam, that is conformable to the shape of the canal and exerts a distributed spring force on the ear canal to hold the retainer in place. Retention in the ear canal also be facilitated by the use of a coating that enhances adhesion between the seal and the canal and/or promotes the in growth of fibrils of endothelial tissue known as asparagines to a selected depth into the coating so as to mechanically retain the seal in the ear canal.

The retainer can also be configured to maintain the health and integrity of the ear canal including the epithelium. That is, the retainer is configured to be atraumatic to the canal epithelium and prevent or minimize infection and inflammation of the epithelium. In various embodiments, this can be accomplished by the use of biocompatible materials and configuring the retainer to exert a force on the epithelium less than the venous return pressure of the epithelial vasculature. The retainer can also be vapor permeable (e.g., air and water vapor) and/or vented to reduce humidity buildup within the ear canal tending to cause infection. Infection resistance can be further enhanced through the incorporation of antimicrobial agents into retainer surface and/or retainer coatings.

Also, the retainer can be configured to provide sufficient acoustical sealing to prevent or minimize feedback resulting from acoustical leakages to the hearing aid microphone from the speaker assembly including when the seal is deformed, for example, due to compression of the ear canal from movement of the head etc. The seal can also configured to produce a selectable offset angle between receiver and the microphone assembly to accommodate the shape of the ear canal and facilitate placement of the hearing aid in the canal. Finally, the seal can be configured to position and retain the speaker assembly of the hearing device as close to the tympanic membrane so as to minimize the volume between the two (i.e., the residual volume) and so as to reduce occlusion effects.

Many embodiments of the retainer include an inner wall having a scalloped or convoluted shape. The scallops can be configured to function as hinged elements which collectively impart a selectable amount of stiffness and conformability to the seal. The scalloped or convoluted shape can be configured to perform a number of functions to facilitate use of the hearing aid when positioned in the ear canal including positioning in the bony portion of the canal. First, they can be configured to uniformly distribute the forces exerted by the ear canal so as to have substantially continuous contact between the seal and the ear canal to prevent acoustical gaps. That is, there is little or no buckling or other pleated deformation of the seal resulting in gaps between the seal and the canal wall. The scallops can also be configured to uniformly distribute the spring forces applied by the retainer to the inner surface of the ear canal to retain the hearing aid in the ear canal and at the same not to exceed the capillary venous return pressure of the vasculature of the epithelial layer of the inner layer of the ear canal.

Also as discussed above, in many embodiments, the retainer can include a coating used to facilitate retention of the seal in the ear canal as well as perform several other functions. The retention function of the coating can be accomplished by several means. First through the use of an adhesive coating configured to adhere to the inner surface of the ear canal. Also the coating can be configured to promote the in-growth of fibrils of endothelial tissue known as asparagines to a selected depth into the coating so as to mechanically retain the seal in the ear canal. In addition to performing a retention function, the coating can be configured to have acoustical attenuation properties so as to increase the acoustical attenuation of the seal. In specific embodiments, the coating can be configured to increase the acoustical attenuation of the seal by about between 5 to 10 decibels or more. Finally, the coating also be a hydrophobic coating configured to perform a sealing function to prevent liquid water from entering into and saturating the retaining seal.

One embodiment provides a seal for retaining a continuous wear hearing device within the bony portion of an ear canal comprising a curved shell having an opening at an apex portion of the shell. The shell can have a dome-like or hemispherical shape that defines a cavity for retention of a hearing device component such as a hearing aid portion of hearing aid such as the microphone assembly. At least a portion of the shell comprises a resilient material having sound attenuating properties. An interior surface of a shell wall has a scalloped or other shape configured to distribute compressive forces applied to the shell perimeter such that when the shell is positioned in the ear canal, the shell wall conforms to the shape of the ear canal to maintain an acoustical seal between an exterior surface of the shell and the walls of the ear canal. When a force is applied to the shell (e.g., by the ear canal), the shell wall conforms to the shape of the ear canal to prevent an acoustical leak between the exterior surface of the shell and walls of the ear canal. The scalloped shape can be configured to produce a substantially constant amount of inward deformation of a shell wall independent of a force application point on a shell perimeter. At least a portion of the shell can include a coating configured to retain the seal in the ear canal and/or to promote asparagine growth into a selected depth into the coating to fastenly retain the seal in the ear canal. The shell can include a sleeve that fits over a portion of the hear aid and a vent positioned on the walls of the shell. The vent can function as one or both of a pressure relief vent or an occlusion relief vent. The shell wall has a gas permeability configured to reduce an incidence of ear canal infection when the seal is positioned in the canal as well as allow substantial equilibrium between a relative humidity in the portion of the ear canal occluded by the seal(s) and a relative humidity of ambient air outside the ear.

Another embodiment provides a method for wearing a hearing device in the ear canal user such as a CIC hearing device. The hearing device includes an embodiment of the seal described herein, wherein the seal is configured to retain the in the ear canal with a force that does not exceed the capillary venous return pressure of a canal epithelial layer. The device is positioned at a location in the ear canal (e.g., the bony portion) and then can be worn in the canal on continuous basis for extended periods of six months or longer without necrosis, ulceration or other irritation of the epithelial layer in that blood flow to or from the ear canal is not impeded by contact with or presence of the seal. The seal serves to retain the device in the canal during head or jaw motion and also substantially maintain an acoustical seal between the seal and the canal wall so as prevent acoustical leaks causing feed back in the hearing device, such as those from the device microphone assembly to a speaker assembly.

Another embodiment provides a method for retaining a hearing device in the ear canal of a user that includes providing a hearing device having a retaining seal including a surface for inducing or promoting the in-growth of biological tissue from the walls of the ear canal. The hearing device can include a CIC hearing device. The hearing device is then positioned in at a location in the ear canal, for example, the bony portion of the ear canal. Desirably the device is positioned deeply in the ear canal so as to minimize the residual volume, but can be position at any selected location in the canal. Growth of biological tissue into the surface of the seal is then induced so as to retain the hearing device at the location. The biological tissue typically include hair-like protrusions known as asparagines which grow a selected depth into the surface. In this way, the in-grown surface functions as a fastening surface and the asparagines as fasteners to retain the surface and thus the hearing device in the ear canal during extended periods of wear, for example, six months or longer. The fastening forces are strong enough to retain the device in the canal during the course of head and jaw movement or other body motions, but still allow the device to be easily removed.

BRIEF DESCRIPTION OF THE DRAWINGS

FIG. 6A shows an embodiment of the seal configured for a hearing aid having a symmetric cap, and FIG. 6B shows an embodiment of the seal configured for a hearing aid having an asymmetric cap.

DETAILED DESCRIPTION OF THE INVENTION

Various embodiments of the invention provide systems, devices and assemblies for improving the durability, comfort and fit of CIC and other hearing devices worn deep in the ear canal on a long term basis. Specific embodiments provide a retaining seal for retaining a CIC hearing aid deep in the ear canal when worn on a long term basis.

Figure 1:
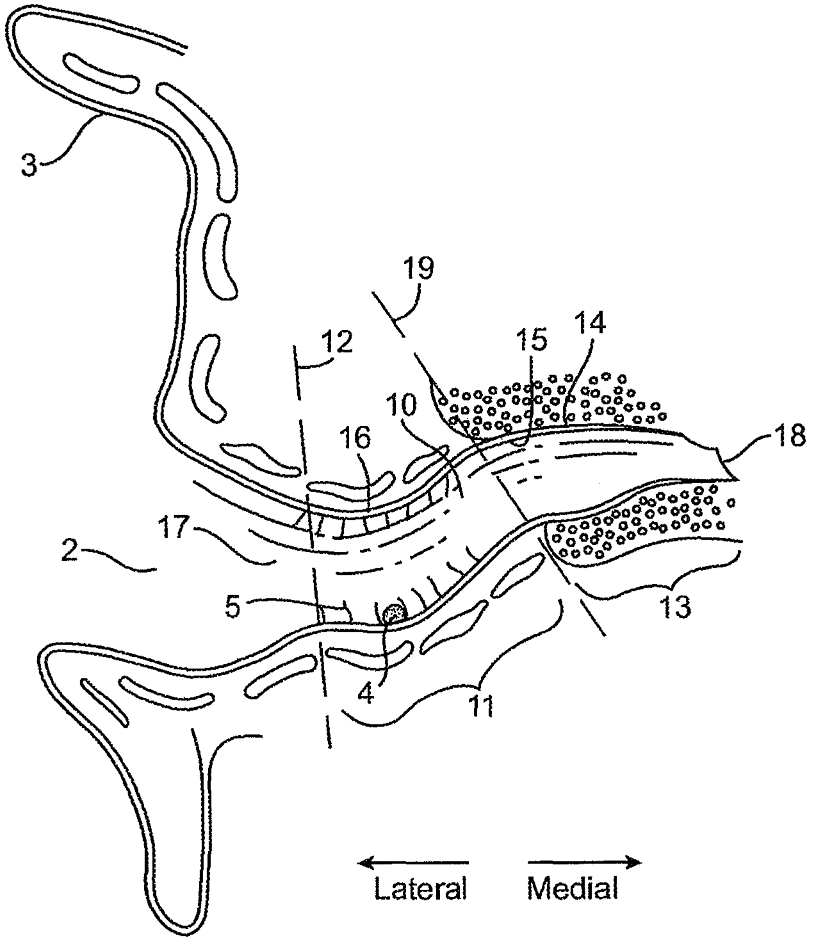
FIG. 1 is a side coronal view of the external ear canal.
Figure 2:
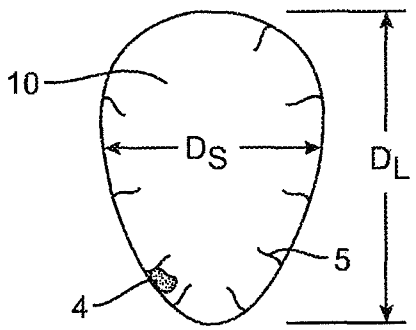
FIG. 2 is a cross-sectional view of the ear canal in the cartilaginous region.
Figure 3:
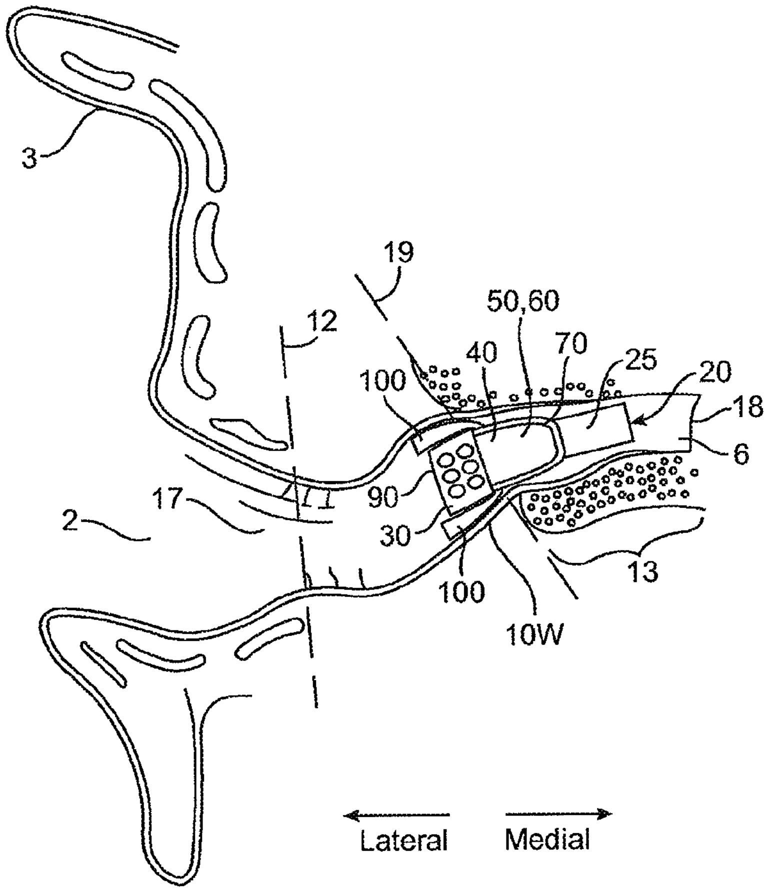
FIG. 3 is a lateral view illustrating an embodiment of a hearing aid device positioned in the bony portion of the ear canal.
Figure 4:
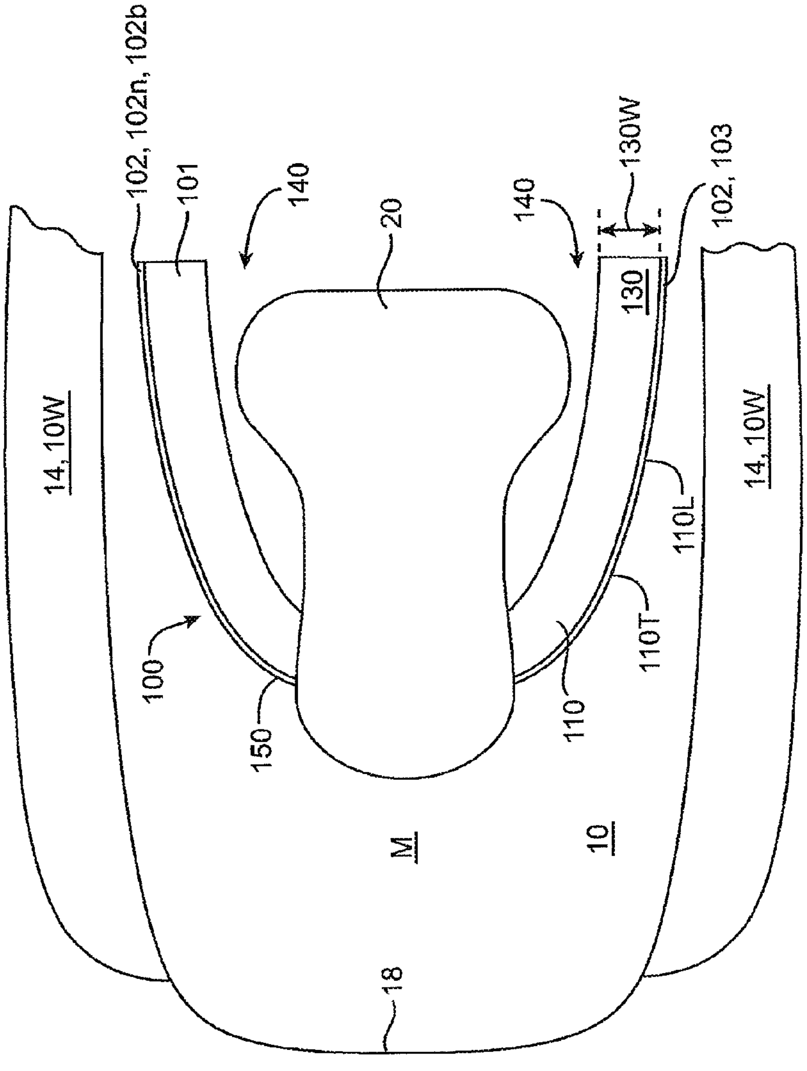
FIG. 4 is a side view illustrating an embodiment of the retainer having a shell and central opening.

Referring now to FIGS. 3-4, an embodiment of a CIC hearing aid device 20 configured for placement and use in ear canal 10 can include a receiver (speaker) assembly 25, a microphone assembly 30, a battery assembly 40, a cap assembly 90 and one or more sealing retainers 100 (also called seal 100) that can be coaxially positioned with respect to receiver assembly 25 and/or microphone assembly 30. Receiver assembly 25 is configured to supply acoustical signals received from the microphone assembly to a tympanic membrane of the wearer of the device. Battery assembly 40 includes a battery 50, and can also include a battery barrier 60 and a battery manifold 70. Preferably, device 20 is configured for placement and use in the bony region 13 of canal 10 so as to minimize acoustic occlusion effects due to residual volume 6 of air in the ear canal between device 20 and tympanic membrane 18. The occlusion effects are inversely proportion to residual volume 6; therefore, they can be minimized by placement of device 20 in the bony region 13 so as to minimize volume 6. Preferably, device 20 is also configured for extended wear in ear canal 10. In specific embodiments, hearing device 20 including a protective cap 90, can be configured to be worn continuously in the ear canal, including the bony portion, for 3 months, 6 months or even longer. Hearing device 20 can include various hearing aids known in the art including, without limitation, ITE, ITC and CIC hearing aids as well assemblies or components thereof e.g., the speaker assembly, etc. For ease of discussion, hearing device 20 will now be referred to as hearing aid 20 (which in many embodiments is a CIC hearing aid configured to be positioned in the bony portion of the ear canal); however, other types hearing devices described here and known in the art are equally applicable.

Figure 5A:
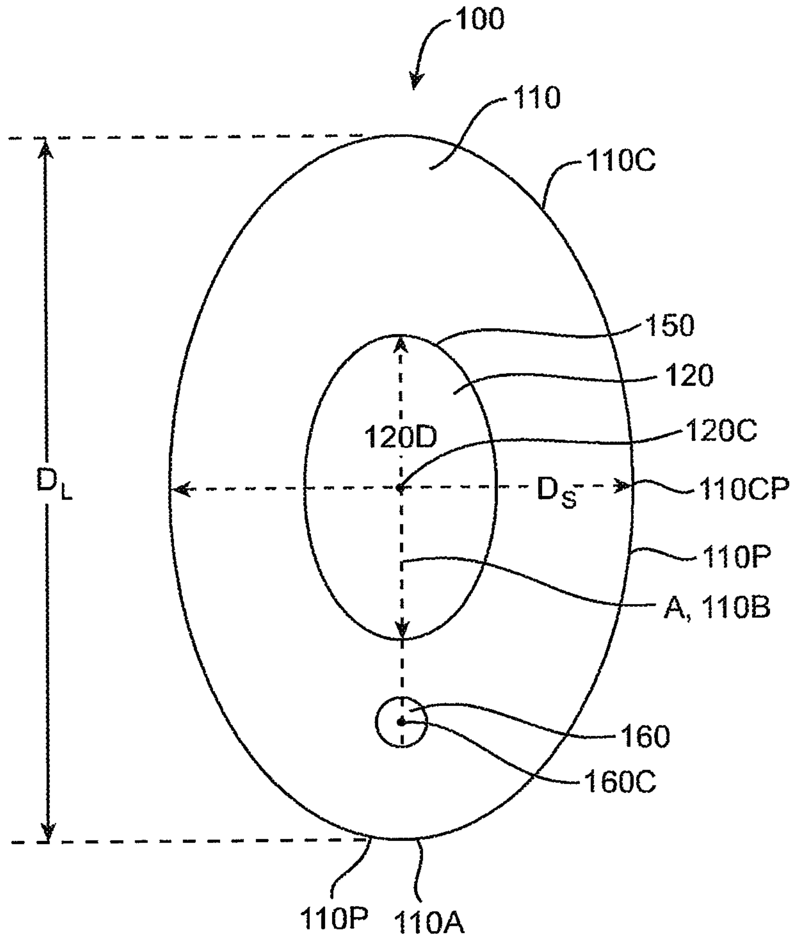
FIG. 5A is a top down view of an embodiment of the seal illustrating the position of the central opening on the apex of the shell and the position of a vent.
Figure 5B:
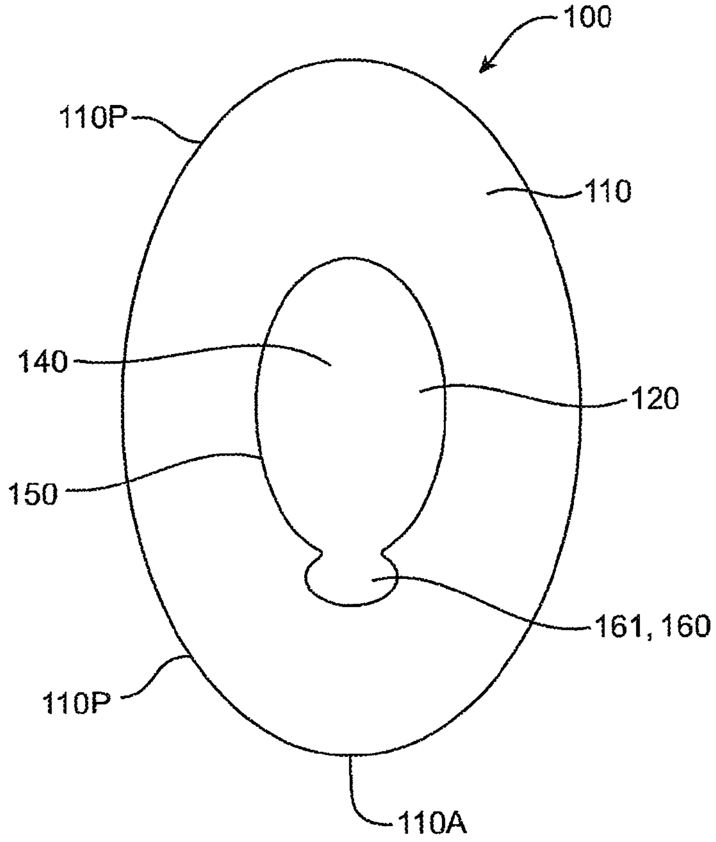
FIG. 5B is a top down view of an embodiment of the seal illustrating having a vent continuous with the central opening of the shell.

Referring now to FIGS. 4-6, a discussion will be presented of a retaining seal used for retaining a hearing device such as CIC hearing aid for continuous wear in the ear canal.

In various embodiments, retaining seal 100 includes a shell 110 having an opening 120, and walls 130 defining a cavity 140 for holding hearing device 20. In preferred embodiment, at least one seal 100 is adapted to be positioned, as shown, substantially in the bony region 13 coaxially over the receiver assembly 25 (or other device portion) of hearing device 20. In other embodiments, the hearing device can include two seals 100/shells 110 mounted over the device, one seal mounted over receiver assembly 25 (or other hearing device portion or component) and another over the battery assembly 40 (or other hearing device portion or component). Seal 100 is configured to provide the primary support for the device 20 within the ear canal 10. The seal is also configured to substantially surround portions of device 20 to protect it from contact with the walls 10W of the ear canal and exposure to cerumen, moisture and other contaminants. To that purpose, seal 100 can be configured to substantially conform to the shape of walls 10W of the ear canal in the bony region 13 and to maintain an acoustical seal between a seal surface and the ear canal and retain the device securely within the ear canal 10. The seal can be configured to be mounted concentrically or non-concentrically over the hearing device. Also the seals can be configured to be mounted over or to specific assemblies or portions of the hearing device, for example, the battery assembly, receiver assembly etc.

Opening 120 can be centrally placed (with respect to shell 110) at a medial apex 110A of the shell 110 and is configured to fit over and retain hearing aid 20 in the ear canal. Preferably, opening 120 is concentric with respect to shell 110 so as to facilitate the centering of hearing aid 20 in the ear canal. However, in alternative embodiments it can be non-concentric. The shape of the opening 120 can be substantially circular or square but is preferably oval. The diameter 120D of opening can be in the range of 0.5 to 1.5 mm with a preferred embodiment of about 1 mm. Also opening 120 can be sized to mounted over specific assembly or portion of the hearing, e.g., the battery assembly, speaker assembly, etc. A vent 160 can be positioned near opening 120. In one embodiment opening and vent centers 120*c* and 160*c* can be aligned on common axis A, which can be a line 110B bisecting shell 110. In another embodiment shown in FIG. 5B, vent 160 can actually be formed in the opening 120, such that opening 120 closes around hearing aid 20, but still leaves an opening 160 for venting. In another embodiment, the opening can include a cutout 161 for a vent-tube that is integral to hearing aid 20.

A discussion will now be presented of the shape and dimensions of the seal 100 and shell 110. The shape and dimension of the seal 100 and shell 110 are desirably selected to allow the seal to comfortably fit in the ear canal and retain a hearing device 20 in the canal for continuous or near continuous long-term wear, e.g. three to six months or longer. The shell 110 has cross sectional and lateral profiles 110C and 110L one or both of which can be configured to approximately correspond to the corresponding profile of ear canal 10. Also both cross sectional and lateral profiles 110C and 110L can be custom fit to the ear canal of the user by making a mold or cast of the ear canal using methods known in the art (e.g. elastomeric or paraffin molding techniques). In an exemplary embodiment, the shell 110 can have a dome like, or hemispherical shape having an apex 150 oriented toward a medial direction M of the ear canal 10. Other volumetric shapes that can be used for shell 110 can include without limitation, ovoid, rectangular, pyramidal, cylindrical or elongated cylindrical.

Also the shape of the shell can be sized for fitting over particular portions of the hearing device. In embodiments of hearing device 20 that include two seals, one seal can include a first shell sized for a first portion of the hearing device (e.g., the battery assembly) and another seal can include a another shell sized for a second portion of the hearing device (e.g., the receiver assembly). The shells and other portions of the seal can also be sized and shaped to perform the same or different function or to enhance a particular function. For example, in one embodiment, one seal can be configured to attenuate sound at a first frequency range and another seal at a second frequency range. In another embodiment, one seal can configured to primarily perform an acoustical attenuation or like function and the other a retaining or like function.

In various embodiments, profile 110C can be oval, elliptical or circular. In a preferred embodiment, profile 110C is oval and includes a short diameter $D_s$ and a long diameter $D_l$ which can be about 1.6 times that of the short diameter $D_s$ in order to approximately correspond to the profile of the ear canal. Also diameter $D_s$ can range from about 4.5 to 9 mm and diameter $D_l$ can range from about 7.25 to 15 mm. Also in this and related embodiment the thickness 130W of shell walls 130 can vary over the perimeter 110P of the shell. For example, the thickness can increase over the central portion 110CP of the shell and decreased at apex's 110A. The varied thickness can be used to achieve desired mechanical properties of the shell, for example circumferentially constant deformation. In specific embodiments, wall thickness 130W can vary from about 0.048" at apex 110A to about 0.055" at the center portion 110CP. Also in specific embodiments, thickness 130W can vary based on a logarithmic, parabolic, second order or other equation with respect to perimeter 110P.

The lateral profile 110 of the shell is desirably configured to produce a comfortable fit in the ear canal while accounting for typical variations in the size and shape of the canal. In various embodiments, the lateral profile 110L can have a medially decreasing taper 110T including a constantly decreasing taper. The taper is desirably configured to produce a lateral profile 110L that approximately corresponds to the lateral profile of the ear canal.

Figure 6A:
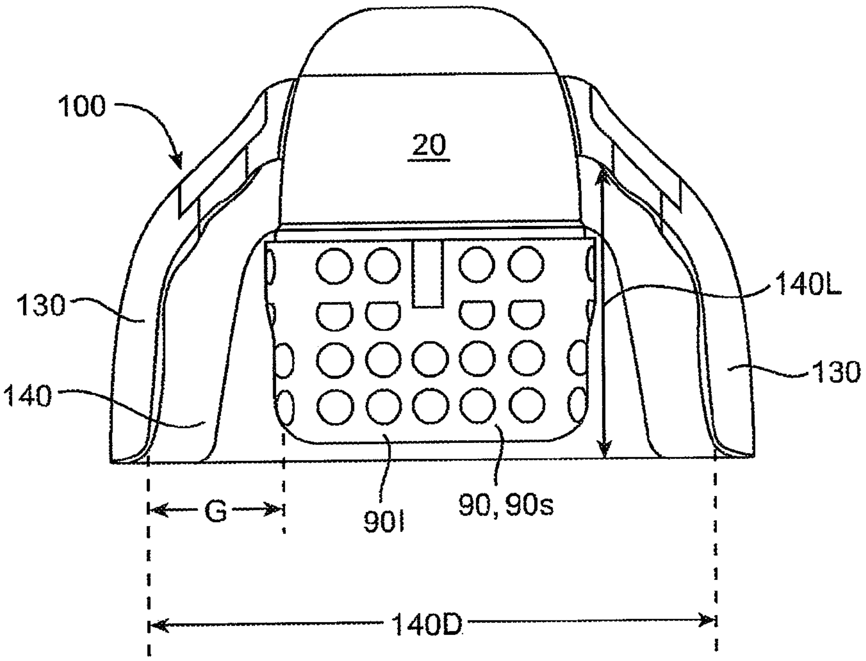
FIGS. 6A-6B are side phantom views illustrating embodiments of the seal positioned over a hearing device.
Figure 6B:
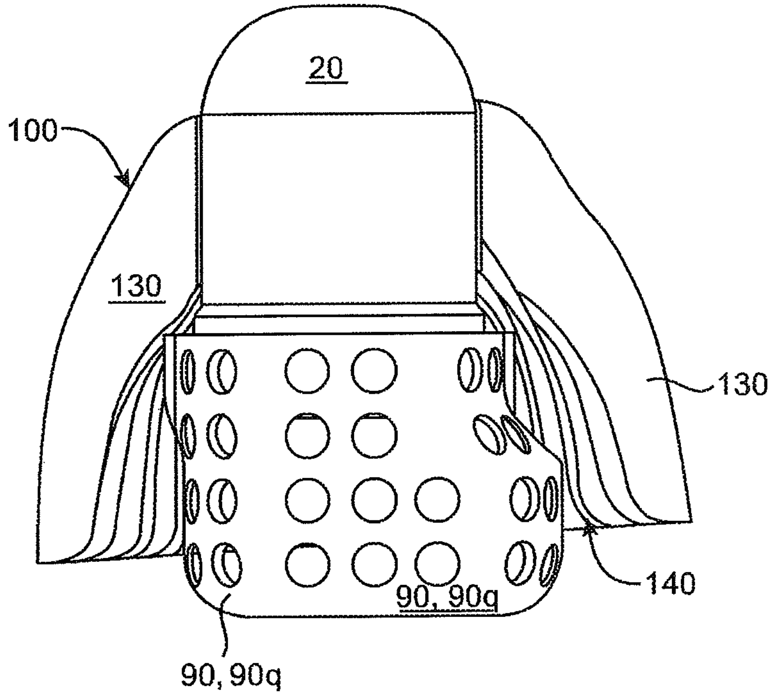

The dimensions of the seal 100 including cavity 130 also desirably selected to accommodate the size and shape of hearing device 20. In particular the inner diameter 140D of cavity 140 can be selected to provide a gap G between hearing aid 20 and the shell walls 130 (see FIGS. 6A and 6B) to provide for ventilation of the hearing aid as is discussed herein. The shell can be configured to provide a greater or lesser gap G depending upon the size and shape of the hearing aid (see FIGS. 6A and 6B). In various embodiments, the shell can be configured to accommodate hearing aids having either a symmetrically aligned cap 90*s* as shown in FIG. 6A or an asymmetrically aligned cap 90*q* as shown in FIG. 6B. Also, the depth 140L of the cavity can be configured such that shell walls 130 laterally extend past the lateral face 901 of cap 90. Desirably, this amount of extension is no more than about 1 mm.

Figure 6C:
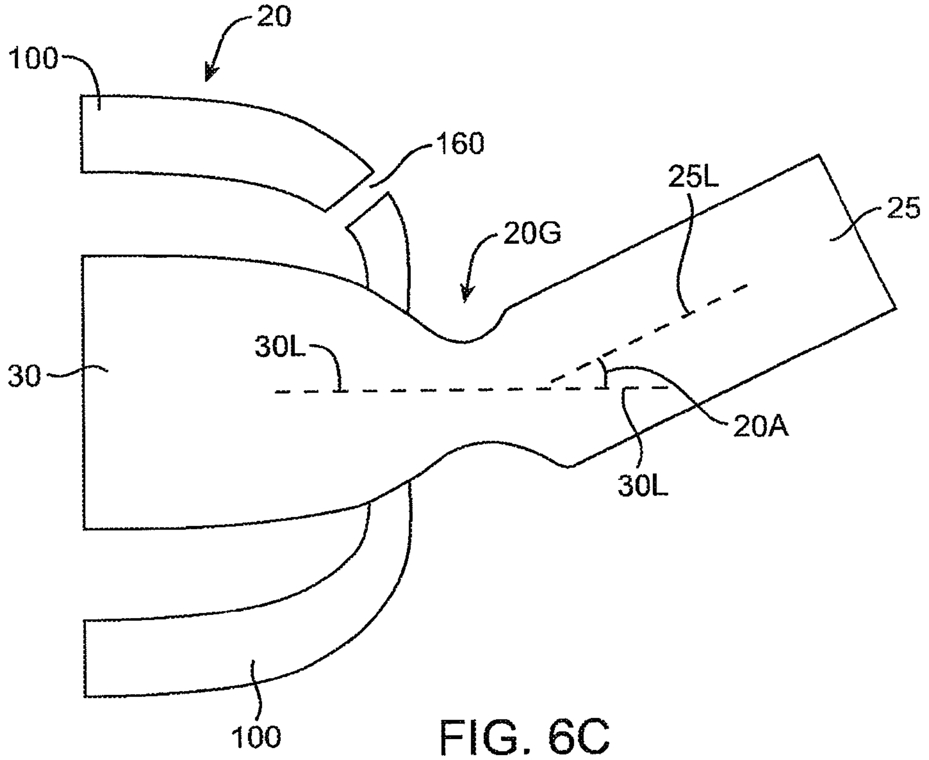
FIG. 6C is a lateral view illustrating an embodiment of the seal configured to hold hearing aid to produce a selectable offset angle between components of the hearing aid.

In various embodiments, in addition to having a shape configured to fit in the ear canal and retain a hearing aid therein, the seal can also be configured to retain one or more components of the hearing aid in a selectable position or angle relative to one another. As illustrated in FIG. 6C, in specific embodiments seal 100 can have a shape configured to retain microphone assembly 30 and receiver assembly 25 at a selectable angle known as offset angle 20A with respect the longitudinal axis of each assembly. The offset angle can also be achieved through the use of two or more seals comprising a multi-seal system as is described below. Offset angle 20A can range from about 10 to 40° with specific values of 15, 25 and 35°. In a preferred embodiment, the seal is configured to produce an offset angle 20A such that longitudinal axis 30L of microphone assembly 30 is oriented 15° anteriorly (i.e. with respect to the nose) with respect to the longitudinal axis 25L of speaker assembly 25. This angle gives hearing aid 20 a banana like shape which serves to accommodate the shape of the ear canal and so improve the fit of the hearing aid in the ear canal both during static and dynamic situations (e.g. during jaw movement). The offset angle 20A also produces a small gap 20G between the microphone assembly 30 and speaker assembly. Gap 20G facilitates the passage (e.g. via diffusion) of oxygen and water vapor around hearing aid 20 improving battery life for embodiments of the hearing aid 20 having metal air batteries and reducing moisture buildup in the ear canal. Also seal 100 can allow offset angle to adjust to account for movement in the ear canal occurring during chewing, talking and other jaw or head movements. Specifically, the seal can be configured to allow the microphone assemblies to bend and/or rotate with respect to each other due deformation of the ear canal from jaw and head motion.

In various embodiments, the shape and material properties of seal 100 and shell 110 can be configured to perform several functions. First, they can be configured to assist in the centering and retention of the hearing device 20 in ear canal 10. Centering can be achieved by configuring opening 120 to be substantially centrally positioned with respect to shell 110. Retention can be achieved by the configuring the seal to exert a spring force (though its shape and use of resilient materials known in the art, e.g., foam elastomers) on the ear canal combined with a surface 102 having a coefficient of friction and/or adhesive quality (through the use of a coating described herein) such that the ear canal exerts a frictional force on the surface of the seal tending to resist the seal being displaced (i.e. laterally displaced) from the ear canal, e.g., due to jaw or head motion, or even epithelial migration. Retention can further be enhanced through the use of a surface coating 103 configured to promote in growth of tissue asparagines so as to fastenly retain the seal in the ear canal. The shape and properties of the seal can also configured to promote the health of the ear canal by configuring the seal not to exert a force on the ear canal which exceeds the capillary venous return pressure of the canal endothelium (about 15 mm Hg). This can be achieved though the selection of the dimensions and compliance (e.g. compression modulus) of the seal. In this way, the seal provides an atraumatic means for retaining a hearing device 20 in the ear canal.

Also in many embodiments, the seal dimensions (e.g. thickness) and materials can be configured to allow sufficient vapor transmission (e.g. permeability) though the seal to prevent or minimize excessive moisture build up in the canal with seal in place. Suitable permeable materials can include without limitation, silicone, polyurethane and other elastomeric foams known in the art. In a preferred embodiment, the seal is fabricated from using a vapor permeably polyurethane foam. Finally, the seal can be configured to provide sufficient acoustical attenuation to prevent or minimize acoustical feedback from the microphone assembly to the speaker assembly. This can be achieved through selection of one or more of the dimensions (e.g. thickness), shape and material properties of the seal. For example, higher levels of attenuation can be achieved through the use of one or both of denser materials or thicker wall dimensions. In various embodiments, seal 100 can be configured to provide between about 10 to 55 dB of acoustical attenuation between the lateral and medial portions of the seal over the range of human audible frequencies. In preferred embodiments, the seal is configured to provide greater than 35 dB of acoustical attenuation and even more preferred embodiments greater than 45 dB of acoustical attenuation.

In various embodiments, the acoustical attenuating properties of the seal can be further enhanced, particularly at selected frequencies, through the use of one or more coatings described herein such as a silicone coating. The coating can be configured to provide greater attenuation over a selected range of frequencies which can partially or fully overlap the attenuation frequency range of the seal or be at a different frequency range altogether. Thus in use, the coating provides a bi or even multi level frequency range of acoustical attenuation. The coating can also be configured (e.g., via control of viscosity, surface tension, etc) to fill in any pores or micro imperfections in the material of the seal than can serve as channels for acoustical leaks and, in this way, serve as a fault tolerant acoustical attenuation layer. Further, the coating can be configured to fill in such imperfections which develop after seal insertion and in this way the coating serves as self repairing acoustical attenuating layer which provides the seal with a self repairing acoustical attenuating property.

Figure 6D:
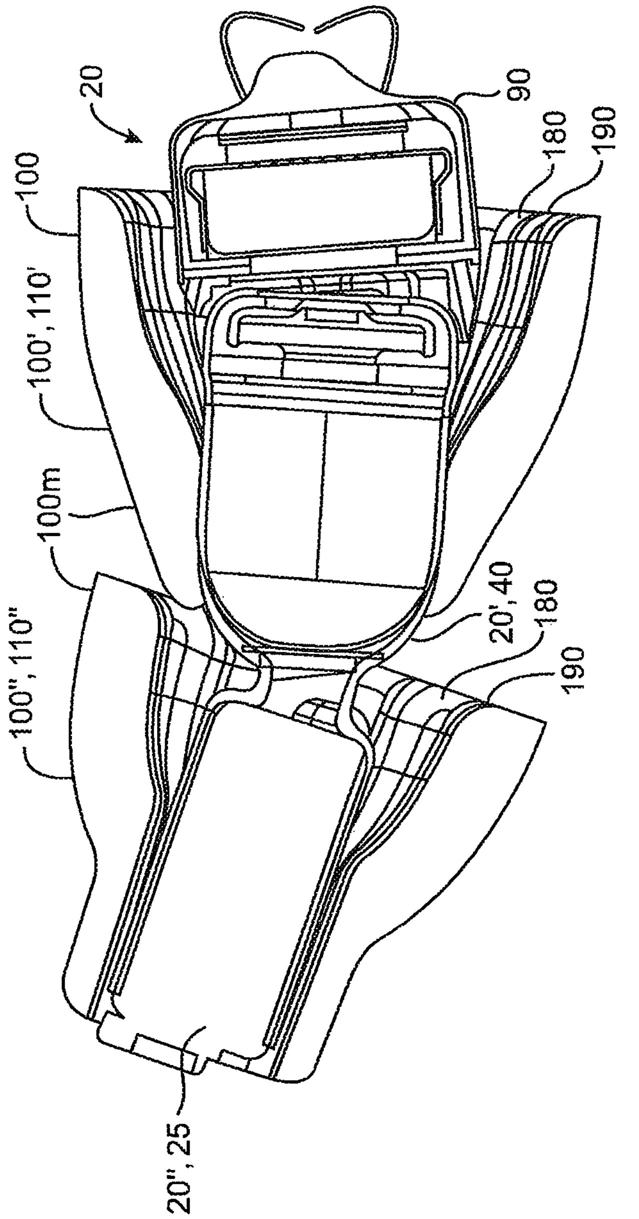
FIG. 6D is a lateral view illustrating an embodiment of the seal having a first and a second seal.

In various embodiments, seal 100 can comprise two or more seals so to form a multi-seal system 100*m*. FIG. 6D shows an embodiment of a multi-seal system 100*m* having a first seal 100' and shell 110' sized to fit a first portion 20' of the hearing device 20 and second seal 100" and shell 110" sized to fit over a second portion 20" of the hearing device. In one embodiment, the first portion 20' can be sized to fit over battery assembly 40 and the second portion receiver assembly 25. As described above, the shells and other portions of the seal can also be sized and shaped to perform the same or different function or too enhance or augment a particular function (e.g., acoustical attenuation). For example, in one embodiment, seal 100' can be configured to attenuate sound at a first frequency range and seal 100' at a second frequency range. Also seal 100" can configured to primarily perform an acoustical attenuation function and seal 100' a retaining function or vice versa. To this end, the seals can have different dimensions and shapes. For example, first seal 100" can have a larger diameter as well as a greater number and different pattern 190 of scallops 180 than second seal 100". In this way, multi-seal 100*m* system provides a multi-functional seal for both retaining and improving the acoustical performance of a hearing device in the ear canal. Seal 100' and 100"can also be configured (e.g., via size, shape, etc) to produce a selected offset angle as is described above.

In various embodiments, the seals of system 100*m* can also be adapted to fit in different parts of the ear canal 10. For example seal 100" can be adapted to be placed more medially in the canal closer to the tympanic membrane and seal 100' more laterally. More specifically, seal 100' can have a shape and spring force to center and retain hearing device first portion 20' (e.g., the battery assembly) in a first location in the ear canal and seal 100" can have a shape and spring force to center and retain hearing device second portion 20"(e.g., the receiver assembly) in a second location in the ear canal. The use of different shapes and spring forces for the seals allows different shaped components of hearing device 20' to be centered and comfortably retained in different portions of the ear canal. It also provides for more points of contact and additive spring force for retaining the hearing device in the ear canal. In this way, the two seals of multi-seal system 100*m* provide a dual spring retention means for more securely and comfortably retaining a hearing device in the ear canal for periods of extended wear.

Figure 7:
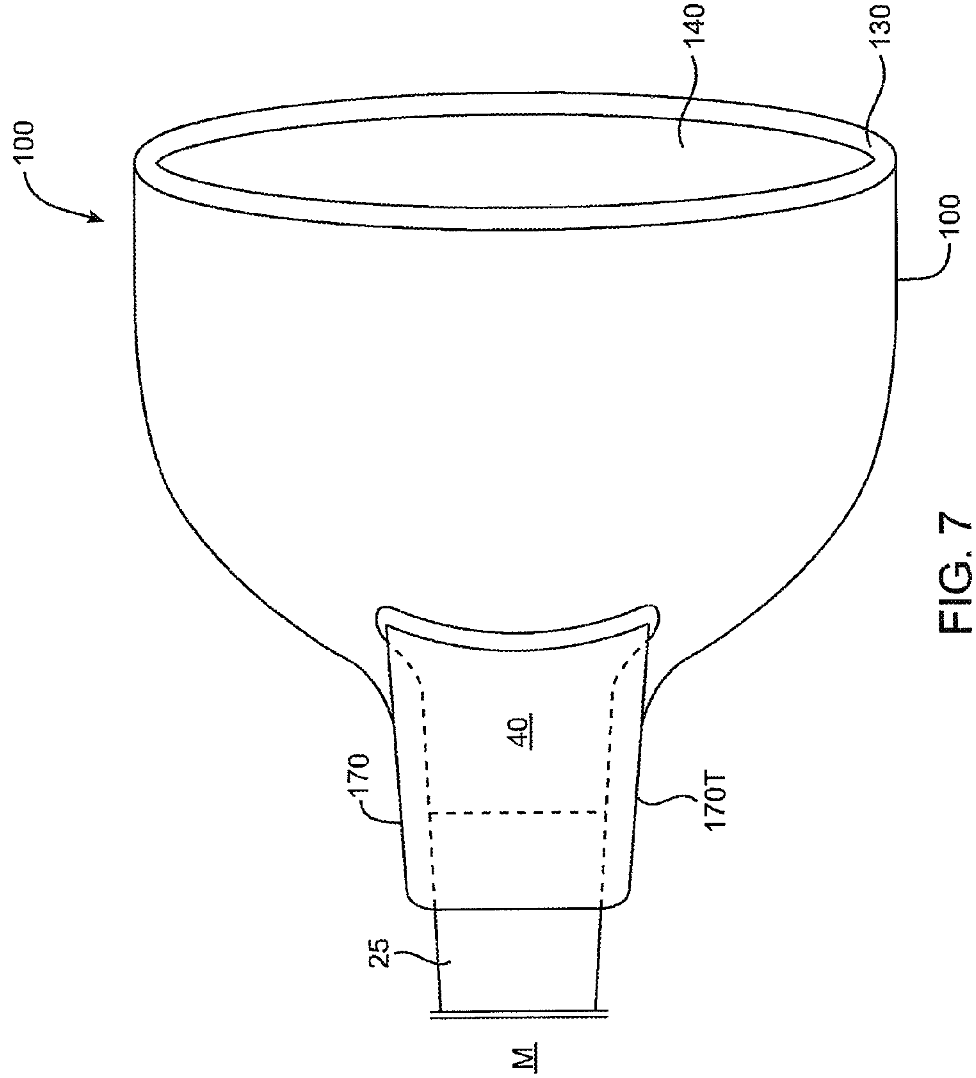
FIG. 7 is a side view which illustrates an embodiment of the shell having an adjoining sleeve.

As shown in FIG. 7, in various embodiments, the shell can be coupled or otherwise include a sleeve or sleeve portion 170 that can be coupled to the shell 110 at opening 120. Sleeve 170 is configured to fit over portions of hearing device 20 such as battery assembly 40 and/or receiver assembly 25. The sleeve can be configured to protect these assemblies as well to help retain and/or stabilize the hearing device within the seal. The sleeve can be circular or oval in cross section and in a preferred embodiment has a rectangular cross section corresponding to the shape of an assembly of hearing aid 20 such as the speaker assembly. Also, all or a portion of the sleeve 170 can have a taper 170T. In one embodiment, taper 170T is a decreasing taper in the medial direction M. In various embodiments, the sleeve can comprise an elastomeric rubber or other complaints material known in the art which is sufficient compliant to stretch over portions of hearing aid 20 and hold it in place by compression.

In various embodiments, all or a portion, of seal 100 can comprises a compliant material configured to conform to the shape of the ear canal. In many embodiments, the seal is fabricated from an elastomeric foam 100*f* having dimensions and compliance properties configured to conform to the shape of the ear canal and exert a spring force on the canal so as to hold the seal 100 in place in the ear canal. Foam 100*f* can be either open cell or closed cell as is known in the art. Suitable materials for foam 100*f* include polyurethanes, silicones, polyethylenes, flouropolymers and copolymers thereof. In a preferred embodiment, foam 100*f* is a polyurethane foam known in the art. Also in various embodiments, all or a portion of seal 100 can comprise a hydrophobic material known in the art including an hydrophobic layer or coating. Also the material while being hydrophobic, can be also be permeable to water vapor transmission. Examples of such material, include without limitation, silicones and flouro-polymers such as expanded polytetroflouroethylene (PTFE).

In various embodiments, seal 100 can include a core portion or core 101 and a skin portion (hereinafter "skin") or surface layer 102. The two portions can comprise different materials or the same material with different properties. In many embodiments, the skin can be substantially smooth and the core porous. Also in many embodiments, the skin is integral to the core portion. However, in alternative embodiments the two can be separate layers with the skin affixed or coated onto the core. In a preferred embodiment, skin 102 comprises a substantially smooth non porous layer 102*n* that is integral to porous core portion 101. This and related embodiments, can be produced by a combination process of injection molding and casting of the seals using polymer processing methods known in the art.

Figure 5C:
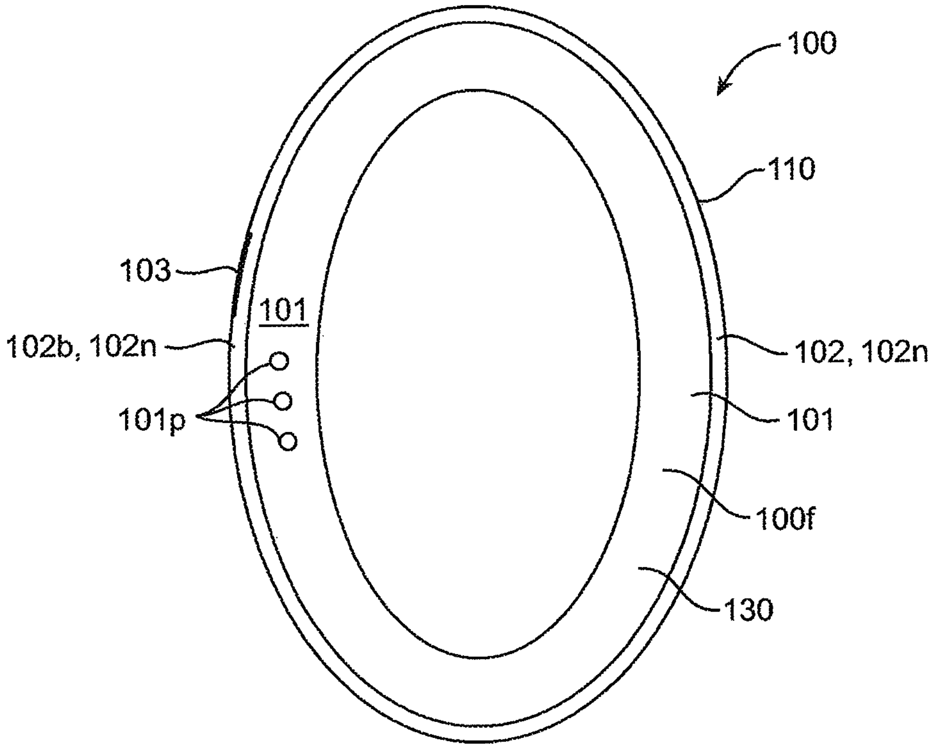
FIG. 5C is a cross sectional view illustrating the structure of the walls of an embodiment of the seal.

In various embodiment layer 102 and layer 102*n* can be configured to perform several functions including one or more of the following: i) retention of the seal in the ear canal; ii) providing a biocompatible tissue contacting layer; iii) providing a barrier to liquid ingress; and iv) providing for the dimensional stability of the seal 100. In particular embodiments, layer 102*n* also serves to seal off the pores 101*p* of core portion 101 so as to form a sealed layer or barrier 102*b* to the influx of water and other liquids into seal 100 including core 101 as is shown in FIG. 5C. In particular, barrier 102*b* can be configured to have sufficient liquid barrier properties to substantially prevent seal 100 including core 101 from swelling after periods of extended wear due to the absorption or ingress of appreciable amounts of water over time. In this way, layer 102*b* serves to maintain the dimensional stability of seal 100 over periods of extended wear, e.g., three to six months or longer. The liquid barrier properties of layer 102*b* can be enhanced by the use of a hydrophobic coating 103. Suitable hydrophobic coatings include medical grade silicone coatings known in the art such as those available from the Dow® Chemical Corporation. While barrier 102*b* serves as a liquid barrier, at the same time it can be configured to permit water vapor transmission though the barrier to allow water vapor to diffuse through the seal. For example, barrier 102*b* can be configured to prevent liquid water from entering the seal but allow water vapor on the medial side of the seal (e.g. due to sweat) to diffuse down gradient to the lateral side to allow the medial side to equilibrate with ambient humidity levels. In this way, the liquid barrier vapor transmission properties of barrier 102*b* serve to reduce the incidence of infection of ear canal 20 and seal 100 by reducing the moisture levels within the seal and/or within the ear canal. The infection resistance of the coating can be further increased through the use of an antimicrobial agent such as silver-oxide or other silver based compounds, known in the art.

Figure 8A:
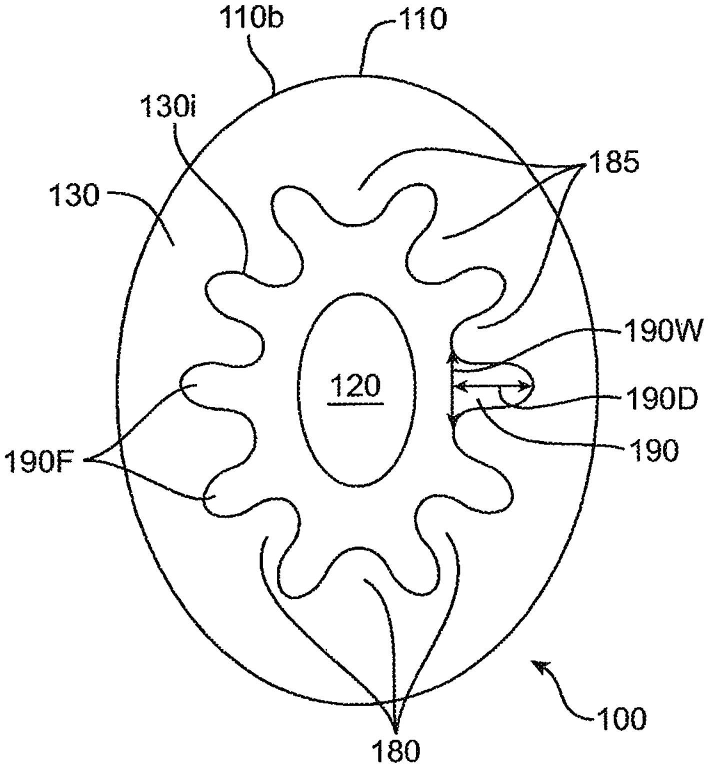
FIG. 8A is a bottom up cross sectional view showing an embodiment of the retainer having scalloped walls.
Figure 8B:
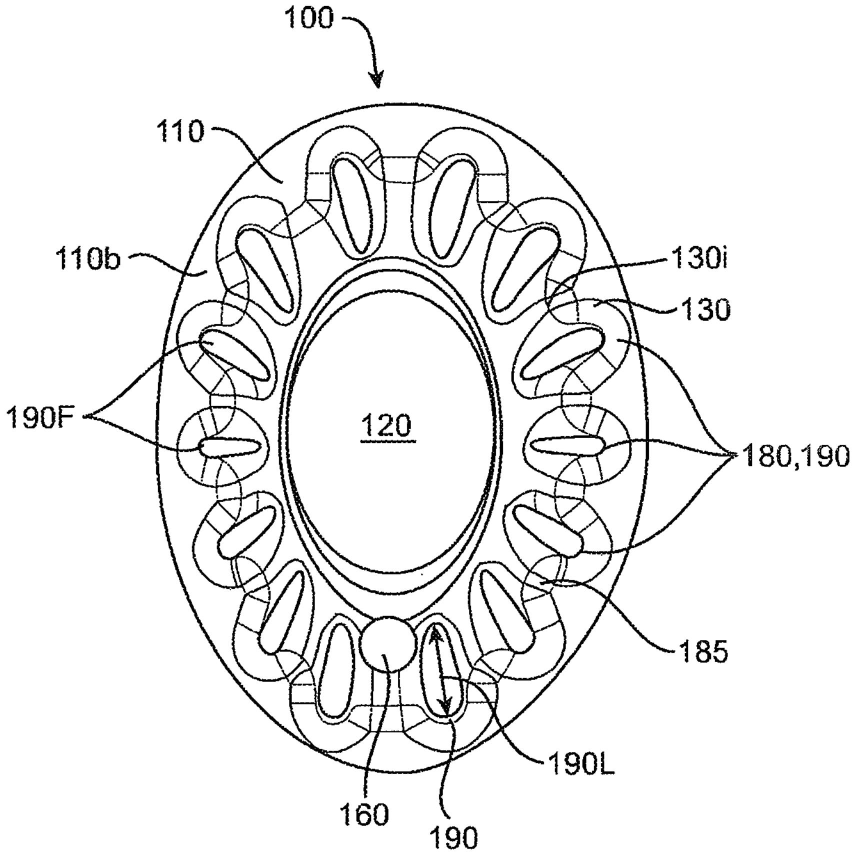
FIG. 8B is a bottom up view showing an embodiment of the retainer having scalloped walls that include vent.
Figure 9:
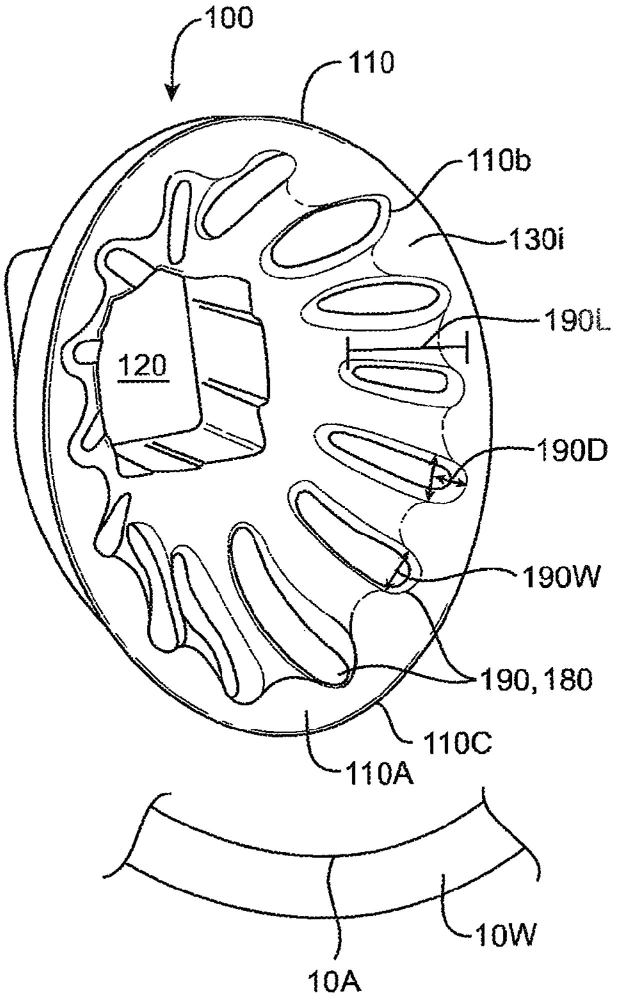
FIG. 9 is a perspective view of another embodiment of the retainer having scalloped walls.

Referring now to FIGS. 8A-8B and 9, in various embodiments the inner portion 130*i* of wall 130 of shell 110 can include a scalloped or convoluted pattern or shape 180 having one or more scallops 190. The scallops can be configured to function as hinged elements 185 which collectively impart a selectable amount of stiffness and conformability to the walls of the seal as well as allowing a number of functions described below. The scallops can have a selectable depth 190D, length 190L width 190W and frequency or pitch 190F (i.e. number of scallops per unit length). These dimension can be configured to impart to each scallop and/or hinge with a selectable stiffness. The length 190L can extend from opening 120 to the base of the shell 110*b* or a shorter distance.

Example scallop patterns 180 are shown in FIGS. 8A-8B and 9. The scalloped patterns can be configured for embodiments of the seal having an oval or round opening 120 as is shown in FIGS. 8A and 8B or rectangular opening 120 as is shown in FIG. 9. Also the scalloped pattern can be configured for embodiments of the seal having a vent as is shown in FIG. 8B. In various embodiments, the number of scallops can range from about 5 to 20, more preferably 6 to 15 and the pitch can be in the range from about 0.010 to 0.060". In one embodiment, the pitch of the scallops can be about 0.030" with the seal having a total of 14 scallops. Also, the scallops can all have the same shape or a different shapes. For example, in one embodiment, the shape of the scallops can alternate every other scallop, with the scallops varying in one or more of length, depth or width. The varying shape of the scallops can be used to produce a circumferentially substantially uniform amount of deformation of the seal as well as a circumferentially substantially uniform application of spring force by the seal on the ear canal. For example, in one embodiment, this can be achieved by having different shaped scallops at the apex 110A of profile 110C corresponding the apex 10A of the ear canal as is shown in FIG. 9. In various embodiments, the shape, pitch and number of scallops can be selected depending upon one or more of the following criteria: i) the shape and dimensions of the ear canal of an individual patient; ii) the shape, dimensions and material properties of the sealing retainer; iii) the shape and dimensions of the hearing aid; iv) whether one or two or more seals are used; and v) where the hearing aid is positioned in the ear canal e.g., the bony portion 13 vs. the cartilaginous portion 11.

Figure 10B:
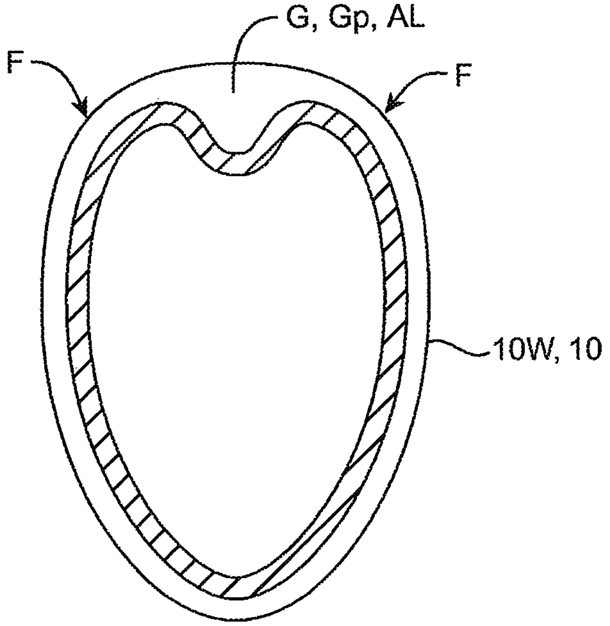
FIG. 10B is a cross-sectional view of an embodiment of the retainer without scalloped walls which illustrates development of a gap or buckling of the seal when positioned in the ear canal as result the application of compressive forces from the canal.
Figure 10A:
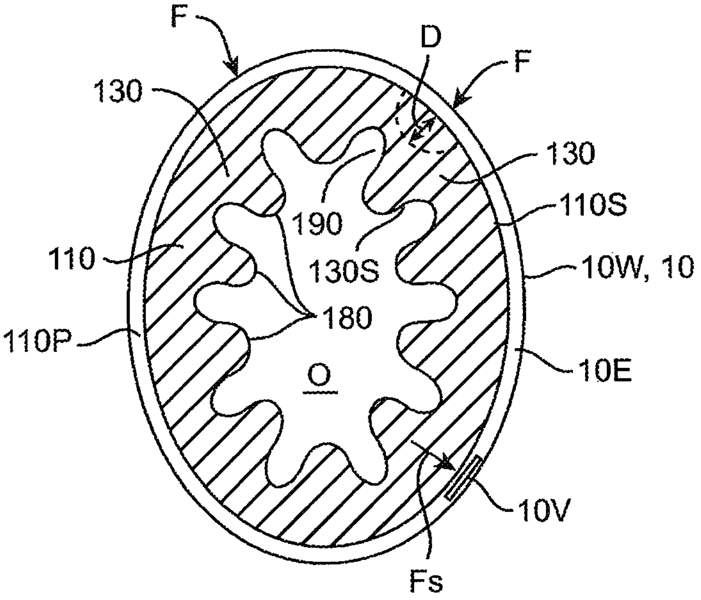
FIG. 10A is a cross-sectional view of an embodiment of the retainer having scalloped walls which illustrates the distribution/applications of compressive forces from the ear canal on the shell wall.

Referring now to FIGS. 10A and 10B, in various embodiments, scalloped pattern 180 can be configured to perform a number of functions. First pattern 180 can be configured to uniformly distribute compressive forces F applied by the ear canal to the shell surface 110S such that there is substantially continuous contact between the seal and the ear canal to prevent acoustical gaps. More specifically, pattern 180 can be configured to distribute the compressive forces F applied to the outer surface 110S of shell wall 130 by canal 10 such that the shell wall 130 does not appreciably deform to cause a gap G resulting in an acoustical leak between an the outer surface of the shell 110S and walls of the ear canal 10W as might occur without the scalloped patterns (See FIG. 10B). In specific embodiments, the scalloped pattern 180 is configured to prevent buckling of the seal including pleated deformation resulting in a pleated gap Gp. Also scalloped shape 180 can be configured to produce a substantially constant amount of inward deformation D of shell wall 130 independent of site of force application along shell perimeter 110P. This results in a more uniform seal between seal 100 and the ear canal.

By uniformly distributing force (e.g., around the perimeter of the seal), scalloped pattern 180 also serves to decrease the amount of deformation and/or compression of the seal in response to forces applied by the ear canal to the seal. This decreased deformation provides several benefits. First, it provides more room in the cavity 140 allowing for a larger space for hearing aid 20 as well as a gap G between the hearing aid 20 and the inner surface 130*s* of the shell walls 130. Providing a larger gap G in turn allows for better ventilation of the inside of the shell reducing moisture buildup as well as facilitating diffusion of air to the battery assembly (improving battery life for embodiments having metal air batteries) and to microphone assembly (improving acoustic performance).

The reduced amount of seal deformation provided by embodiments of the seal having scallops 190 also serves to improve the vapor transmission of the seal including water vapor transmission. The improvement in water vapor transmission is due to several factors. First there is less reduction in the porosity of the seal walls due to compression of the shell walls. That is, because there is less compression/deformation fewer channels or pores (not shown) of the seal walls become occluded as a result of deformation. Also the density of wall 130 is not increased as much as would be for larger amounts of deformation, this improves the permeability of the wall. Finally, vapor transmission of embodiments of the seal having scallops 190 is increased because the wall thickness 130W of the seal can be decreased. As discussed herein, improved water vapor transmission reduces the likelihood of moisture buildup in ear canal and so reduces risk of infection due to such moisture. Specific embodiments of scalloped pattern 180 can be configured to maximize water vapor transmission by minimize wall deformation and/or compression of the shell walls.

In addition to uniformly distributing the application of forces by the ear canal on the seal, the scallop pattern can also be configured to uniformly distribute the application of spring force Fs (e.g., normal) exerted by the seal on the inner circumference of the ear canal. This results in a greater degree of comfort for the patient by preventing the concentration of force in particular locations in the canal which can cause pain or irritation to the wearer. The prevention of force concentration also reduces the development of skin irritation and/or ulceration at such locations as well as preventing degradation of the bony portion of the ear canal (i.e. lost bone mass) for devices positioned therein. Further, scallop pattern 180 can be configured such that force Fs exerted by the seal on the canal does not exceed the capillary venous return pressure of the vasculature 10V of the canal epithelial layer 10E. This pressure is approximately is approximately 15 mm Hg. To stay under this pressure, seal 100 is desirably configured to exert no more than about 5 grams and more preferably no more than about 1.2 grams of force on the ear canal for 1 mm of deflection of the seal with a lower level of about 0.1 to 0.6 grams. As is discussed herein, this configuration serves to facilitate the long term health of the ear canal by reducing or preventing tissue ulceration and/or necrosis of the canal epithelium due to occlusion of the vasculature of the epithelium and thus preserve the health and structural integrity of the epithelium in contact with the seal. In this way, the scalloped shape of the inner seal wall serves to improve one or more of the comfort, biocompatibility and wearability of an extended wear hearing device 20 retained by seal 100 in the bony portion of the ear canal.

Figure 11A:
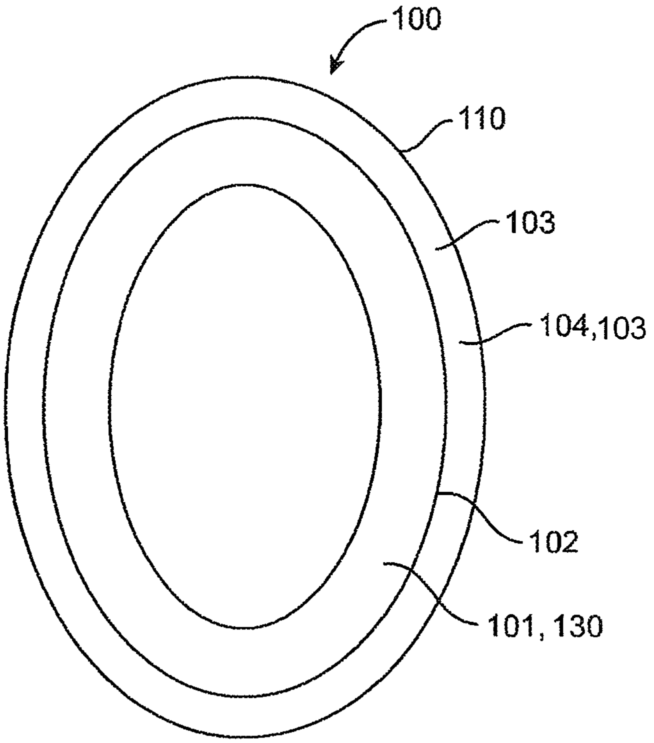
FIG. 11A is side view illustrating an embodiment of the seal having a coating.
Figure 11B:
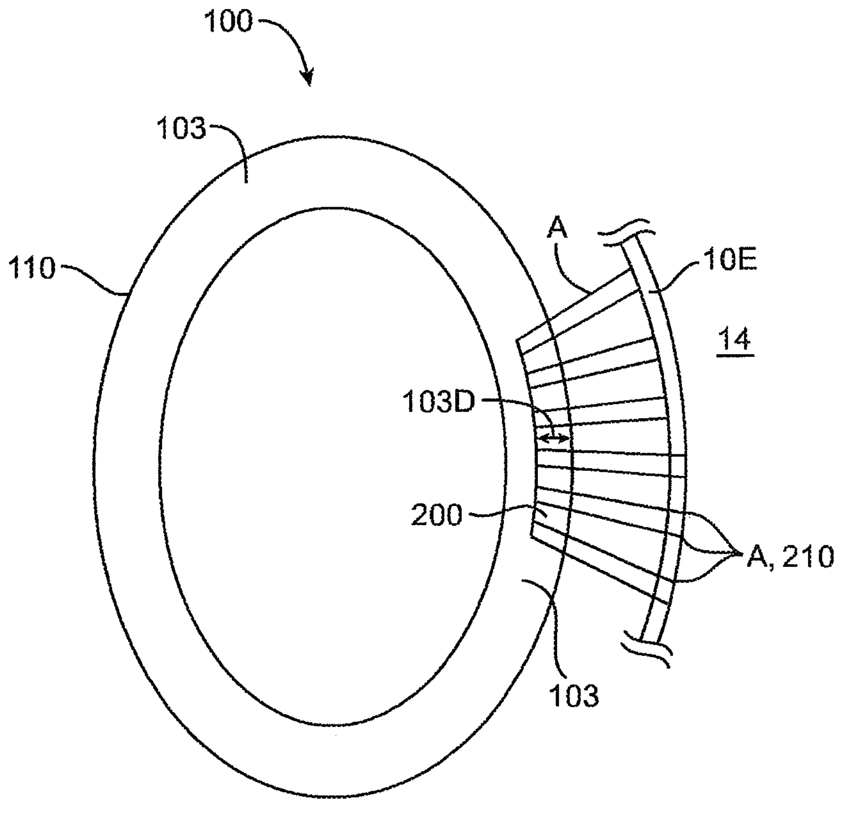
FIG. 11B is a side view illustrating in-growth of asparagines into coating of the seal

Referring now to FIGS. 11A and 11B, in many embodiments, all or a portion of seal 100 can include a coating 103. Coating 103 can configured to facilitate or otherwise enhance retention of the seal in the ear canal as well as perform several other functions. The retention function of the coating can be accomplished by several means. First, coating 103 can be an adhesive coating 104 configured to adhere to the inner surface of the ear canal. Suitable adhesive coatings include biocompatible silicones adhesive coatings known in the art (e.g., silicone adhesives available from the General Electric Corporation). Such coatings can be configured to have a sufficient amount of adhesive force to retain the seal in the ear canal, but also be releasable to allow the user or physician to readily be able to remove the seal by hand and/or with the aid of an extraction tool.

Also the coating can be configured to promote the ingrowth of fibrils of endothelial tissue known as asparagines A to a selected depth 103D into the coating so as to mechanically retain the seal in the ear canal. Used in this way, coating 103 functions as a fastening surface 200 and asparagines A function as mechanical fastening elements 210. Together, these components function to fastenly retain seal 100 in the ear canal. In many embodiments, coating/surface 103 can be configured to retain the seal in the ear canal both through adhesive means (e.g. where the coating is an adhesive coating) and through mechanical fastening means. In this way, the use of coating 103 provides a dual means of retention of the seal in the ear canal for enhanced and thus more reliable retention of an extended wear hearing device in the ear canal.

In addition to performing a retention function, coating 103 can also be configured to have acoustical attenuation properties so as to increase the acoustical attenuation of the seal. In various embodiments, the coating can be configured to increase the acoustical attenuation of seal 100 in a range between about 1 to 10 decibels, with specific embodiments of 3 and 5 decibels. Also, the coating can be configured to produce different amounts of acoustical attenuation by varying one or more of the viscosity/or filler components of the coating. For example, increased attenuation can be achieved by increasing the viscosity of the coating or increasing the concentration of particles within the coating. For silicone coatings, silica fillers can be used, or a silica free solution can be employed. Also, as described above, in particular embodiments the coating can be configured to fill in any pores or micro imperfections in the surface or core of the seal (initially present or that develop post implant) that may act as channels for acoustical leakage. In this way, the coating serves as an acoustical attenuation fault tolerance layer as well as a self repairing acoustical attenuating layer. Finally, the coating can also be a hydrophobic coating configured to provide or enhance the liquid sealing function of barrier 102*b* as described above to prevent vapor or liquid water from entering into and/or saturating the retaining seal.

Coating 103 also can be configured to provide both dimensional stability and structural integrity of the seal. This can be accomplished by i) configuring the seal to serve as a barrier to moisture and/vapor ingress as described above and ii) configuring the seal to have sufficient circumferential spring force (e.g. hoop elastic modulus, hoop strength) such that the seal material exerts a circumferential force that reduces or prevents seal core 100 from swelling radially or otherwise, for example due to saturation by water or other liquid. This latter property can be specifically achieved by configuring the coating such that the circumferential spring force or hoop strength of the coating exceed any swelling forces of the seal core caused saturation of the core from aqueous solutions. In various embodiments, the circumferential spring force or hoop strength of the seal can be between 0.05 to 0.25 lbs. The configuration of the coating can include one or more of the thickness, elasticity, viscosity and other visco-elastic properties of the coating. In essence, the coating acts as a retaining band or support that opposes any swelling forces of the seal core. This band or support function of the seal in turn thus prevents or reduces the seal from swelling (e.g. in diameter or other dimension) as a result of saturation by water, sweat or other liquids in the ear canal. For use of polymeric coating, such as silastic coatings, increased hoop modulus and/or hoop strength can be obtained by increasing the amount of the cross-linking of the coating (e.g. by thermal or other curing). Through the use of cross-linking, the hoop elastic modulus can titrated for the needs of particular wearer.

The coating can also be configured to provide structural stability to the seal core of the seal by acting as a structurally supporting and protective shell or skin. This shell provides mechanical support (e.g. by hoop strength) to the seal core as well as serving as protective barrier to prevent degradation of the core by chemical environment in the ear canal (e.g. sweat, cerumen, etc). The protective function of the seal is particularly useful for embodiments of the comprising the seal comprising a foam core which can be degraded by the chemical environment within the ear canal due to ingress of liquid and other contaminants into the pores or cells of the foam. In this way, the coating provides a means for extending the life of the seal in the ear canal for periods of continuous extended wear, for example for periods of three to six months or longer without appreciable degradation in the function or structure of the seal. This in turn provides a seal which can be used for extended wear hearing device which can be worn for three to six months or longer.

Figure 12A:
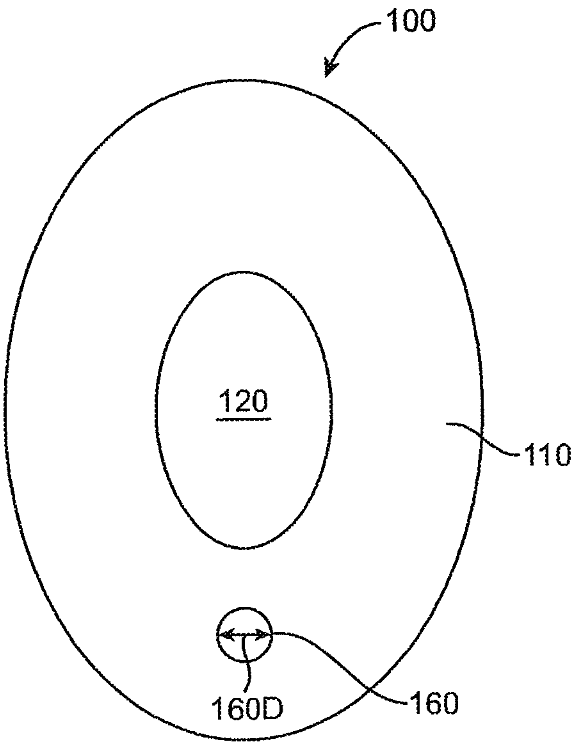
FIG. 12A is top down view showing an embodiment of the seal having a vent positioned close to the central opening.
Figure 12B:
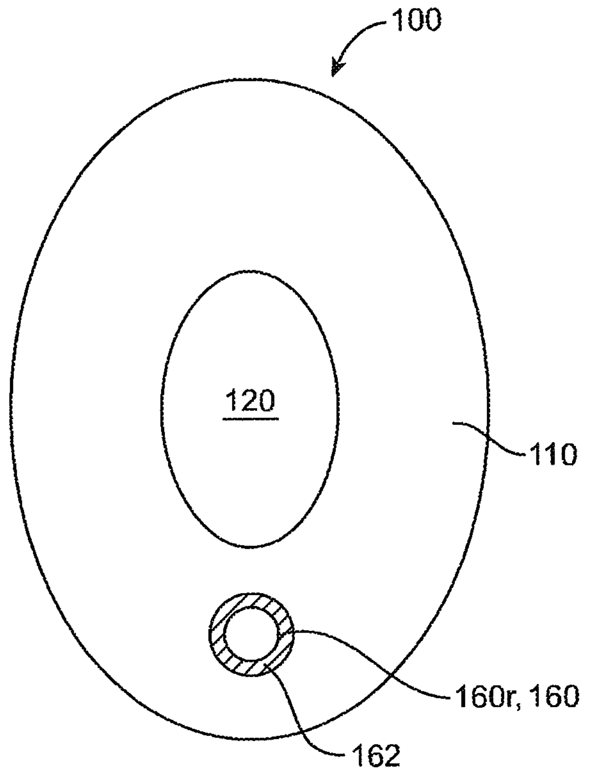
FIG. 12B is perspective view showing an embodiment of the seal having a recessed vent).

Referring now to FIGS. 12A-12B, in many embodiments seal 100 includes a vent 160 configured to allow the passage of air from portions of the canal medial to the seal to those portions lateral to the seal and vice a versa. Vent 160 is preferably positioned on the walls of shell 110 but can also be integral to opening 120 as describe herein. In a preferred embodiment, the vent is positioned on the shell walls close to opening 160. Vent 160 is desirably configured as a pressure relief device to provide rapid pressure equalization during insertion and removal of the hearing aid or during changes in atmospheric pressure. The vent can also allow for ventilation to the medial portions of the ear canal to prevent excessive moisture buildup during periods of extended wear. Additionally, the vent can also be configured as an occlusion relief vent to minimize occlusion effects. Also, the calibration algorithms of hearing aid 20 can configured to account for the size and position of the vent on the seal to further reduce occlusion effects.

In various embodiments, vent 160 can have a circular, or square shape, which can be tapered inward or outward. Also, vent 160 and can be partially recessed within shell 110 to facilitate comfort to the user as is shown in FIG. 12B. In one embodiment, a recessed vent 160*r* can be configured using a lip or chamfer162. In preferred embodiments, vent 160 has a circular shape. The diameter 160D of the vent can range from about 0.0001" to about 0.002." The diameter of the vent can also be configured to allow the passage of air for pressure equilibration but substantially inhibit the passage of liquid water and other fluids due to surface tension factors. In such embodiments, the diameter 160D can be between about 0.0001 to about 0.0008". Vent 160 can be formed by micromachining and/or laser drilling methods known in the art.

In alternative embodiments, vent 160 can include a valve (not shown) configured to regulate air entering and exiting the ear canal. The valve can be micro-valve or MEMs devices known in the art. For embodiments having a MEMs based valve, the valve electronics can be electronically coupled to and/or controlled by electrical components or module of the hearing aid 20, e.g. a processor of the microphone assembly 30. Such regulation equalizes pressure between the ear canal and an external ambient pressure while minimizing acoustical feedback. The valve can be formed as a flap on the sound port. The valve can also be formed as a hinged valve mounted within the sound port.

Conclusion

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the protective seal can be used on a number of hearing devices including ITC devices. Further, the teachings of the invention have broad application in the hearing aid device field as well as other fields which will be recognized by practitioners skilled in the art. For example, various embodiments of seal materials and surfaces configured for asparagine in-growth are also applicable to the field of vascular prosthetics, including vascular grafts, where it is desirable to have tissue in-growth into the graft or other prosthetic in order to stabilize the graft and promote long term biocompatibility and reduced risk of infection. Other embodiments can be configured for use with other medical implants where it is desirable to have tissue in-growth to both stabilize the implant and promote long term biocompatibility. Such applications can include without limitation subcutaneous access ports (e.g., venous and arterial access); long term in dwelling catheters; implantable pumps (e.g., insulin pumps); implantable balloons (e.g. for treatment of aneurisms, gastrointestinal applications, etc.); implantable surgical fabrics, meshes and membranes (e.g. for tissue support and repair); and other like devices and materials.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand alone elements. Hence, the scope of the present invention is not limited to the specifics of the described embodiments, but is instead limited solely by the appended claims.

What is claimed is:

1. A multi seal system for retaining an extended wear hearing device within a bony portion of an ear canal, the system comprising:
at least a first seal and a second seal, at least one of the seals including a curved shell having a shell wall and defining an apex portion, an opening at the apex portion, a cavity for retention of a hearing device component, and a longitudinal axis, the shell wall having an inwardly facing interior surface and an outwardly facing exterior surface and being formed at least in part from a resilient material having sound attenuating properties, and the inwardly facing interior surface of the shell wall having a longitudinally extending scalloped shape configured to distribute compressive forces applied to a shell perimeter.

2. The system of claim 1, wherein the first seal is configured to be coupled to a first hearing device component and the second seal is configured to be coupled to a second hearing device component.

3. The system of claim 2, wherein the first component is a receiver assembly and the second component is at least one of a battery or a microphone assembly.

4. The system of claim 2, wherein the seals retain the first and second hearing device components in the ear canal at an angular offset with respect to each other.

5. The system of claim 2, wherein the first seal exerts a first spring force to retain the first device component at a first location in the ear canal and the second seal exerts a second spring force to retain the second device component at a second location in the ear canal.

6. The system of claim 2, wherein the first seal centers the first device component at a first location in the ear canal and the second seal centers the second device component at a second location in the ear canal.

7. The system of claim 1, wherein the second seal augments the acoustical attenuation of the first seal.

8. The system of claim 1, wherein the first seal attenuates sound at a first frequency range and the second seal attenuates sound a second frequency range.

9. The system of claim 1, wherein the first seal is sized to be positioned at first location in the ear canal and second seal is sized to be positioned at a second location in the ear canal.

10. A system for retaining a hearing device within an ear canal, the system comprising:
a first seal and a second seal, the first seal including
a curved shell having a shell wall formed at least in part from a resilient material having sound attenuating properties, the shell wall defining an apex portion, an opening at the apex portion, an outer surface that is configured to abut the ear canal, and an interior surface that defines a cavity for a first portion of the hearing device, the shell wall interior surface having a plurality of indentations that extend into the shell wall toward the outer surface such that each indentation defines an open end and a close end and the closed end is closer to the outer surface than the open end.

11. A system as claimed in claim 10, wherein the second seal includes
a curved shell having a shell wall formed at least in part from a resilient material having sound attenuating properties, the shell wall defining an apex portion, an opening at the apex portion, an outer surface, and an interior surface that defines a cavity for a second portion of the hearing device, the shell wall interior surface having a plurality of indentations that extend into the shell wall toward the outer surface.

12. A system as claimed in claim 11, wherein
the shell wall of the first seal is formed from a resilient material that attenuates sound at a first frequency range; and
the shell wall of the second seal is formed from a resilient material that attenuates sound a second frequency range.

13. A system as claimed in claim 10, wherein the plurality of indentations define a scalloped shape.

14. A system as claimed in claim 10, wherein the plurality of indentations are configured to distribute compressive forces applied to the outer surface of the shell wall.

15. A system as claimed in claim 10, wherein the outer surface of the shell wall tapers downwardly from the apex portion.

16. A system as claimed in claim 10, wherein
the first seal defines first and second longitudinal ends; and
the first seal includes an openings at the first and second longitudinal ends.

17. A system as claimed in claim 10, wherein the first seal is configured to be coupled to a first hearing device component and the second shell is configured to be coupled to a second hearing device component.

18. A system as claimed in claim 10, wherein
the shell wall includes a core portion and an outer skin; and
the core portion and the outer skin are formed from the same material.

19. A system as claimed in claim 10, wherein
the shell wall includes a core portion and an outer skin; and
the core portion and the outer skin are formed from different materials.

20. A system as claimed in claim 10, wherein the shell wall defines a thickness that is not constant.

21. A system as claimed in claim 10, wherein
the first seal defines a longitudinal axis; and
the outer surface defines a perimeter that is oval in shape in a plane perpendicular to the longitudinal axis.

22. A system as claimed in claim 10, wherein the first seal is sized to be positioned at first location in the ear canal and second seal is sized to be positioned at a second location in the ear canal.

23. A system as claimed in claim 10, wherein the shell wall interior surface defines a circumference and the plurality of indentations are circumferentially spaced.

24. A system as claimed in claim 23, wherein the curved shell defines a longitudinal axis and the plurality of indentations extend longitudinally.

* * * * *